US00PP37826P2

(12) United States Plant Patent
van Dijk

(10) Patent No.: US PP37,826 P2
(45) Date of Patent: Oct. 27, 2026

(54) ***ANTHURIUM* PLANT NAMED 'AN2501852'**

(50) Latin Name: *Anthurium andreanum*
Varietal Denomination: AN2501852

(71) Applicant: ANTHURA B.V., Bleiswijk (NL)

(72) Inventor: Jan van Dijk, Bleiswijk (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 19/559,932

(22) Filed: Mar. 6, 2026

(51) Int. Cl.
*A01H 5/02* (2018.01)
*A01H 6/10* (2018.01)

(52) U.S. Cl.
USPC ..... Plt./368

(58) Field of Classification Search
USPC ..... Plt./263.1, 365, 368
See application file for complete search history.

(56) References Cited

U.S. PATENT DOCUMENTS

PP36,272 P2 * 11/2024 van Dijk ..... Plt./365

* cited by examiner

*Primary Examiner* — Karen M Redden
(74) *Attorney, Agent, or Firm* — C. Anne Whealy

(57) ABSTRACT

A new and distinct cultivar of *Anthurium* plant named 'AN2501852', characterized by its compact, upright to outwardly arching plant habit; freely clumping growth habit; bushy and dense plants; narrowly deltoid to narrowly ovate dark green-colored leaves; freely flowering habit; inflorescences that are positioned above the foliar plane on sturdy scapes; broadly ovate spathes that are dark reddish brown to almost black in color; and spadices that are light orange in color with yellowish green-colored apices.

2 Drawing Sheets

Figure 1:
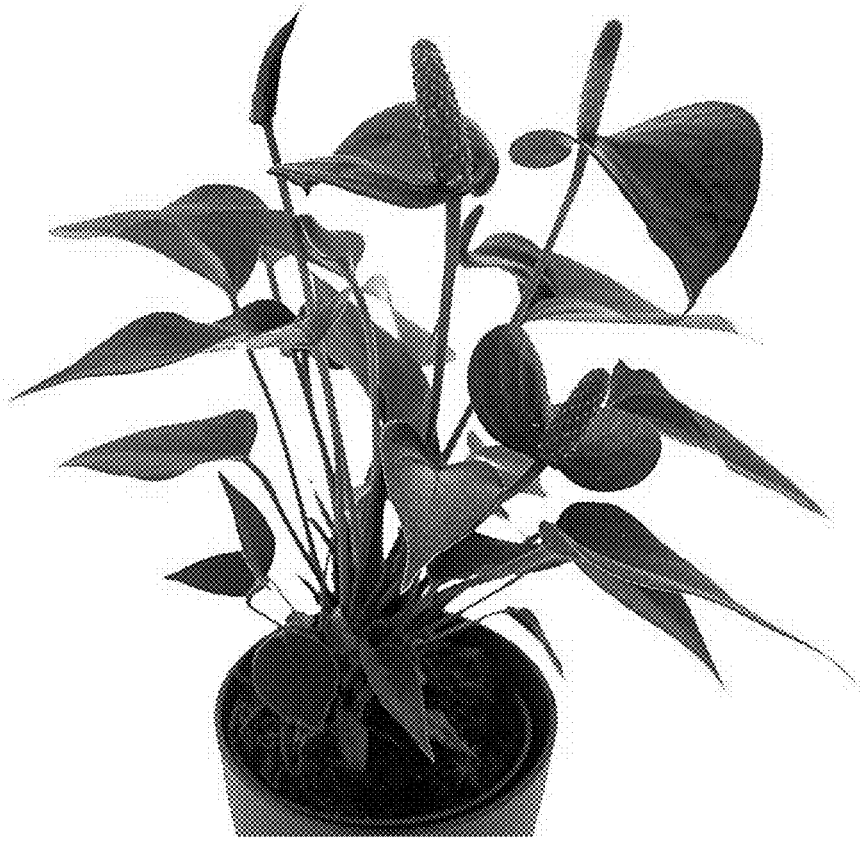

Botanical designation: *Anthurium andreanum.*
Cultivar denomination: 'AN2501852'.

STATEMENT REGARDING PRIOR DISCLOSURES BY APPLICANT

A European Community Plant Breeder's Rights application for the instant plant was filed by the Applicant/Assignee of the instant application, Anthura B.V. of Bleiswijk, The Netherlands on Nov. 20, 2024, application number 2024/2680. Foreign priority is not claimed to this application.

BACKGROUND OF THE INVENTION

The present invention relates to a new and distinct cultivar of *Anthurium* plant, botanically known as *Anthurium andreanum*, commonly referred to as Flamingo Flower and hereinafter referred to by the name 'AN2501852'.

The new *Anthurium* plant is a product of a controlled breeding program conducted by the Inventor in Bleiswijk, The Netherlands. The objective of the breeding program is to create new compact *Anthurium* plants with durable dark reddish brown-colored spathes.

The new *Anthurium* plant originated from a cross-pollination made by the Inventor in January, 2018 in Bleiswijk, The Netherlands of a proprietary breeding selection of *Anthurium andreanum* identified as code number 14-038290-0002, not patented, as the female, or seed, parent with a proprietary breeding selection of *Anthurium andreanum* identified as code number 14-038389-0001, not patented, as the male, or pollen, parent. The new *Anthurium* was discovered and selected by the Inventor as a single flowering plant within the progeny of the stated cross-pollination in a controlled greenhouse environment in Bleiswijk, The Netherlands in August, 2019.

Asexual reproduction of the new *Anthurium* plant by in vitro meristem propagation in a controlled environment in Bleiswijk, The Netherlands since February, 2021 has shown that the unique features of this new *Anthurium* are stable and reproduced true to type in successive generations of asexual reproduction.

SUMMARY OF THE INVENTION

Plants of the new *Anthurium* have not been observed under all possible combinations of environmental conditions and cultural practices. The phenotype may vary somewhat with variations in environment conditions such as temperature and light intensity, without, however, any variance in genotype.

The following traits have been repeatedly observed and are determined to be the unique characteristics of 'AN2501852'. These characteristics in combination distinguish 'AN2501852' as a new and distinct *Anthurium* plant:

1. Compact, upright to outwardly arching plant habit.
2. Freely clumping growth habit; bushy and dense plants.
3. Narrowly deltoid to narrowly ovate dark green-colored leaves.
4. Freely flowering habit.
5. Inflorescences that are positioned above the foliar plane on sturdy scapes.
6. Broadly ovate spathes that are dark reddish brown to almost black in color.
7. Spadices that are light orange in color with yellowish green-colored apices.

Plants of the new *Anthurium* differ primarily from plants of the female parent selection in the following characteristics:

1. Spathes of plants of the new *Anthurium* are not as glossy as spathes of plants of the female parent selection.
2. Spathes of plants of the new *Anthurium* are dark reddish brown to almost black in color whereas spathes of plants of the female parent selection are dark red in color.
3. Spadices of plants of the new *Anthurium* are shorter than spadices of plants of the female parent selection.

Plants of the new *Anthurium* differ primarily from plants of the male parent selection in the following characteristics:

1. Plants of the new *Anthurium* are more compact than plants of the male parent selection.
2. Spadices of plants of the new *Anthurium* are not as tapering as spadices of plants of the male parent selection.

Plants of the new *Anthurium* can also be compared to plants of *Anthurium andreanum* 'AN2142228', disclosed in U.S. Plant Pat. No. 36,272. In side-by-side comparisons, plants of the new *Anthurium* differ primarily from plants of 'AN2142228' in the following characteristics:

1. Spathes of plants of the new *Anthurium* are narrower than spathes of plants of 'AN2142228'.
2. Spadices of plants of the new *Anthurium* are light orange in color with yellowish green-colored apices whereas spadices of than plants of 'AN2142228' are dark reddish brown to dark red in color.

BRIEF DESCRIPTION OF THE PHOTOGRAPHS

The accompanying photographs illustrate the overall appearance of the new *Anthurium*. The photographs show the colors as true as it is reasonably possible to obtain in colored reproductions of this type. Colors in the photographs may differ slightly from the color values cited in the detailed botanical description which accurately describe the colors of the new *Anthurium*.

The photograph on the first sheet (FIG. 1) is a side perspective view of a typical plant of 'AN2501852' grown in a container.

Figure 2:
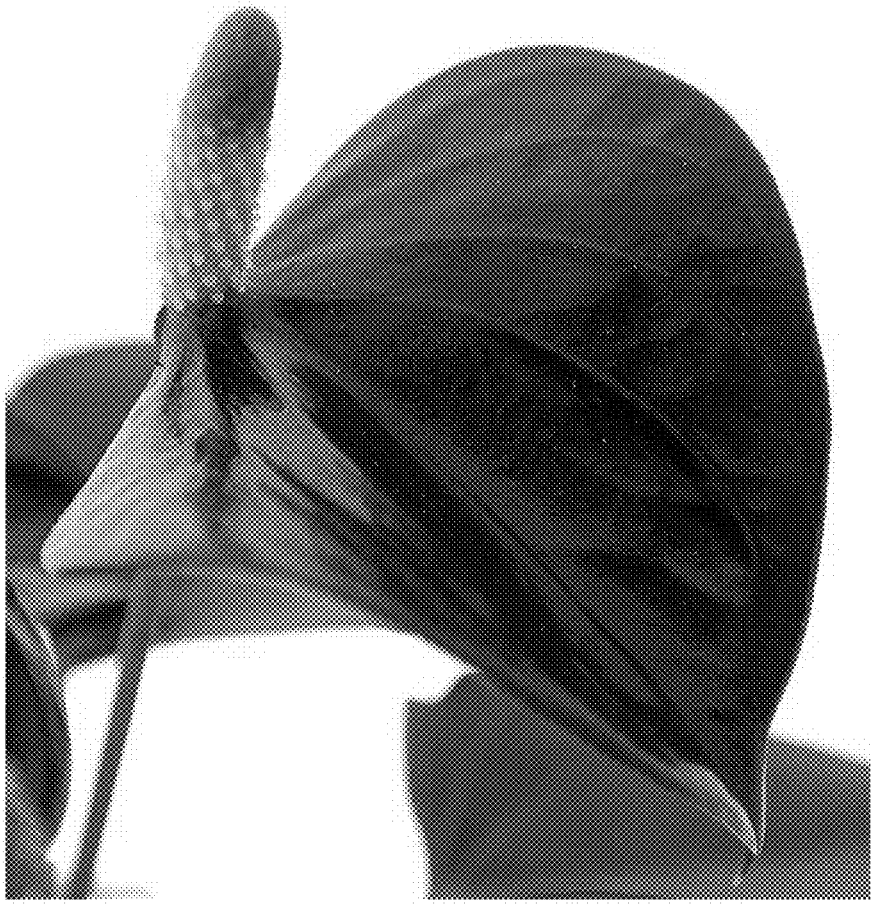

The photograph on the second sheet (FIG. 2) is a close-up view of a typical inflorescence of 'AN2501852'.

DETAILED BOTANICAL DESCRIPTION

The aforementioned photographs and following observations and measurements describe plants grown in 9-cm containers during the early autumn in a glass-covered greenhouse in Bleiswijk, The Netherlands. Plants were grown under conditions and practices which approximate those generally used in commercial *Anthurium* production. During the production of the plants, day and night temperatures ranged from about 19° C. to about 22.5° C. and light levels ranged from about 100 μmol to about 200 μmol. Plants were nine months from planting young rooted plants when the photographs and the detailed description were taken. In the following description, color references are made to The Royal Horticultural Society Colour Chart, 2015 Edition, except where general terms of ordinary dictionary significance are used.

Botanical classification: *Anthurium andreanum* 'AN2501852'.

Parentage:

*Female, or seed, parent*.—Proprietary breeding selection of *Anthurium andreanum* identified as code number 14-038290-0002, not patented.

*Male, or pollen, parent*.—Proprietary breeding selection of *Anthurium andreanum* identified as code number 14-038389-0001, not patented.

Propagation:

*Type*.—By in vitro meristem propagation.

*Time to initiate roots, summer and winter*.—About two weeks at temperatures ranging from about 19° C. to about 22.5° C.

*Time to produce a rooted young plant, summer and winter*.—About six to eight weeks at temperatures ranging from about 19° C. to about 22.5° C.

*Root description*.—Medium in thickness, fibrous; typically creamy white in color; actual color of the roots is dependent on substrate composition, water quality, fertilizer type and formulation, substrate temperature and physiological age of roots.

*Rooting habit*.—Freely branching, medium density.

Plant description:

*Plant shape*.—Compact, upright to outwardly arching plant habit; overall shape, broadly oblong to broadly obovate.

*Growth habit*.—Freely clumping habit imparting a bushy and dense appearance; in a single year of production, about 40 individual plants can be harvested per plant; moderately vigorous growth habit and moderate growth rate.

*Plant height, from soil level to top of leaf plane*.—About 18.1 cm.

*Plant height, from soil level to top of inflorescences*.—About 21.5 cm.

*Plant diameter or spread*.—About 26.8 cm.

Leaf description:

*Arrangement*.—Alternate; simple.

*Length*.—About 9.5 cm.

*Width*.—About 5.3 cm.

*Shape*.—Narrowly deltoid to narrowly ovate.

*Apex*.—Narrowly apiculate with a small mucronate tip.

*Base*.—Cordate.

*Margin*.—Entire; slightly and coarsely undulate.

*Texture, upper and lower surfaces*.—Smooth, glabrous; moderately coriaceous.

*Venation pattern*.—Pinnate.

*Color*.—Developing leaves, upper surface: Close to a blend of 146A and 147A; narrow marginal edges, close to 177A; mucronate tip, close to 165B. Developing leaves, lower surface: Close to a blend of 146A and 148A; narrow marginal edges, close to 177A; mucronate tip, close to 165B; main vein, close to 176A; secondary venation, close to N200A and N200B. Fully expanded leaves, upper surface: Close to a blend of 139A and 147A; narrow marginal edges, close to 143B; mucronate tip, close to 144B; venation, close to 143A and 143B. Fully expanded leaves, lower surface: Close to 146A; mucronate tip, close to 144B; venation, close to 146A.

*Petioles*.—Length: About 9.3 cm. Diameter: Distally, about 2 mm and proximally, about 3 mm. Texture, upper and lower surfaces: Smooth, glabrous. Color, upper surface: Close to a blend of 137D and 138A. Color, lower surface: Close to 144A. Geniculum length: About 1.4 cm. Geniculum diameter: About 3 mm. Geniculum texture, upper and lower surfaces: Smooth, glabrous. Geniculum color, upper surface: Close to 174A and 174B. Geniculum color, lower surface: Close to 146A and 146B. Wing length:

About 1.2 cm. Wing diameter: About 3 mm. Wing texture: Smooth, glabrous. Wing color, upper and lower surfaces: Close to 199A.

Inflorescence description:

*Inflorescence arrangement and flowering habit.*—Spathes with spadices; open inflorescences held above the foliar plane on sturdy scapes; flowering structures arise from leaf axils; freely and continuous flowering year-round in controlled temperature greenhouses in The Netherlands; typically about seven developing and developed inflorescences per plant at one time; inflorescence development commences about 2.5 to 3.5 months after planting rooted young plants.

*Inflorescence longevity*.—On the plant, depending on temperature, spathes maintain good substance for about two months; inflorescences persistent.

*Fragrance*.—None detected.

*Spathes*.—Length: About 5.7 cm. Width: About 5.6 cm. Shape: Broadly ovate to close to reniform; slightly to moderately carinate. Apex: Acute with a short mucronate apex. Base: Shallowly cordate to truncate. Margin: Entire; coarsely undulate. Aspect: About 60° to 100° from the scape axis. Texture, upper and lower surfaces: Smooth, glabrous; moderately coriaceous. Color: When developing, front surface: Close to a blend of 187A and 200B; mucronate tip, close to 150B; areas adjacent to main vein, close to 187B. When developing, rear surface: Close to 178A; towards the base, tinged with close to 152A and 152B; narrow marginal edges, close to 183A; mucronate tip, close to 150B; main vein, close to 183A. Fully developed, front surface: Close to a blend of 200A and 203A; towards the apex, close to 200A; narrow marginal edges, close to 187A; mucronate tip, close to 149A; with subsequent development, color becoming closer to 200A with venation, close to 146b. Fully developed, rear surface: Close to 152A; towards the apex, close to 200C and 200D; narrow marginal edges, close to 183A; mucronate tip, close to 149A; main vein, close to 183A; with subsequent development, color becoming closer to 152C, towards the apex, tinged with closer to 200C and 200D, marginal edges, closer to 200D; mucronate tip, closer to 150C and main vein, closer to 185A.

*Spadices*.—Length: About 3.4 cm. Diameter: About 8 mm. Shape: Cylindrical, slightly tapering towards the apex; apex, obtuse; base, obtuse; in cross-section, rounded. Aspect: Erect to about 40° from the scape axis. Color, immature: Close to a blend of 152A and N199A; towards the base, close to 146A; at the apex, close to 151A. Color, mature: Close to 170C; towards the base, close to N144D; at the apex, close to 146B. Flowers: Type: Hermaphroditic. Quantity per spadix: About 150. Height: About 1 mm. Diameter: About 2 mm. Shape: Roughly square. Anther color: Close to 170C. Pollen amount: Scarce. Pollen color: Close to 155A. Stigma color: Close to 147D. Ovary color: Close to 143C.

*Scapes*.—Length: About 13.9 cm. Diameter: About 2.5 mm. Strength: Sturdy. Aspect: About 25° from vertical. Color: Close to 143A; distally, close to 175A and 175B.

*Seed and fruit*.—To date, seed and fruit development has not been observed on plants of the new *Anthurium*.

Pathogen & pest resistance: To date, plants of the new *Anthurium* have not been observed to be resistant to pathogens or pests common to *Anthurium* plants.

Temperature tolerance: Plants of the new *Anthurium* have been observed to be tolerant to high temperatures of about 30° C. and to be hardy to USDA Hardiness Zone 10.

It is claimed:

1. A new and distinct *Anthurium* plant named 'AN2501852' as herein illustrated and described.

* * * * *